(12) United States Patent
Sato (10) Patent No.: US 9,766,437 B2
(45) Date of Patent: Sep. 19, 2017

(54) OBJECTIVE OPTICAL SYSTEM FOR ENDOSCOPE

(71) Applicant: OLYMPUS CORPORATION, Hachioji-shi, Tokyo (JP)

(72) Inventor: Shinya Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/332,182

(22) Filed: Oct. 24, 2016

(65) Prior Publication Data

US 2017/0038563 A1    Feb. 9, 2017

Related U.S. Application Data

(63) Continuation of application No. PCT/JP2015/078195, filed on Oct. 5, 2015.

(30) Foreign Application Priority Data

Oct. 30, 2014   (JP) ................................. 2014-221109

(51) Int. Cl.
*G02B 13/04* (2006.01)
*G02B 7/105* (2006.01)
(Continued)

(52) U.S. Cl.
CPC ............. *G02B 13/04* (2013.01); *G02B 7/105* (2013.01); *G02B 9/60* (2013.01); *G02B 23/243* (2013.01)

(58) Field of Classification Search
CPC .......... G02B 13/04; G02B 7/105; G02B 9/60; G02B 23/243
(Continued)

(56) References Cited

U.S. PATENT DOCUMENTS 7,907,352 B2    3/2011   Miyano
7,978,423 B2    7/2011   Takato
(Continued)

FOREIGN PATENT DOCUMENTS

JP     2008107391 A    5/2008
JP       4675348 B2    4/2011
(Continued)

OTHER PUBLICATIONS

International Search Report (ISR) and Written Opinion dated Dec. 22, 2015 issued in International Application No. PCT/JP2015/078195.
International Preliminary Report on Patentability (IPRP) (and English translation thereof) dated May 11, 2017 issued in counterpart International Application No. PCT/JP2015/078195.

*Primary Examiner* — James Greece
(74) *Attorney, Agent, or Firm* — Holtz, Holtz & Volek PC (57) ABSTRACT

There is provided an objective optical system for endoscope with a lesser number of lenses and high-performance optical characteristics, equipped with a long back focus and a focusing function, and in which the aberration fluctuation accompanied by focusing is small.
The objective optical system for endoscope includes in order from an object side, a first group having a negative refractive power, a second group having a positive refractive power, and a third group having a positive refractive power, wherein the third group includes in order from the object side, a positive cemented lens and a positive lens, and observation from a normal observation state up to a close observation state is possible by moving the second group along an optical axis and the first group includes a cemented lens, and the first group includes in order from the object side, a negative lens having a concave surface directed toward an image side, and the cemented lens, and the cemented lens is a negative cemented lens, and the second group includes a positive meniscus lens having a convex surface directed
(Continued)

toward the object side, and the objective optical system for endoscope satisfies the following conditional expression (1).

$$4 \leq FB/f \leq 7 \quad (1)$$

where,

FB denotes a hack focus of the objective optical system for endoscope, and f denotes a focal length of the overall objective optical system for endoscope in the normal observation state.

4 Claims, 9 Drawing Sheets

(51) Int. Cl.
*G02B 9/60* (2006.01)
*G02B 23/24* (2006.01)

(58) Field of Classification Search
USPC .................................. 359/749–756, 761, 770
See application file for complete search history.

(56) References Cited

U.S. PATENT DOCUMENTS

| 8,203,798 B2 | 6/2012 | Takato |
| 9,459,443 B2 | 10/2016 | Uzawa et al. |
| 2008/0180809 A1 | 7/2008 | Igarashi |
| 2011/0211267 A1 | 9/2011 | Takato |
| 2012/0057251 A1 | 3/2012 | Takato |
| 2013/0155212 A1 | 6/2013 | Kamo |
| 2013/0217965 A1 | 8/2013 | Sasamoto |

FOREIGN PATENT DOCUMENTS

| JP | 4819969 B2 | 11/2011 |
| JP | 2012037768 A | 2/2012 |
| JP | 4919419 B2 | 4/2012 |
| JP | 5607278 B1 | 10/2014 |
| JP | 2015036778 A | 2/2015 |
| WO | 2010119640 A1 | 10/2010 |
| WO | 2011070930 A1 | 6/2011 |
| WO | 2012169369 A1 | 12/2012 |
| WO | 2013021744 A1 | 2/2013 |

OBJECTIVE OPTICAL SYSTEM FOR ENDOSCOPE

CROSS-REFERENCE TO RELATED APPLICATION

The present application is a continuation application of PCT/JP2015/078195 filed an Oct. 5, 2015 which is based upon and claims the benefit of priority from Japanese Patent Application No. 2014-221109 filed on Oct. 30, 2014; the entire contents of which are incorporated herein by reference

BACKGROUND OF THE INVENTION

Field of the Invention

The present invention relates to an image forming (objective) optical system which can be used in an endoscope apparatus used in a medical field or an industrial field.

Description of the Related Art

Endoscope is an apparatus Which is used widely in the medical field and the industrial field. In the medical field, images of various sites inside a body cavity are achieved by an endoscope inserted inside the body cavity. Diagnosis of a site observed is carried out by using these images. In such manner, endoscopes have been used for observation and diagnosis of various sites inside the body cavity.

In an objective optical system for endoscope, an optical member such as a prism may be disposed in an optical path. Therefore, in the objective optical system for endoscope, sometimes a long back focus is necessary. Objective optical systems having such long back focus have been proposed in Japanese Patent Publication No. 4919419 and Japanese Patent Publication No. 4675348.

Moreover, in endoscopes, increasing the number of pixels of an image pickup element has been progressing in recent years. It is necessary to make an optical spot formed by an optical system all to deal with the increase in the number of pixels. However, if increasing the number of pixels is not dealt with, a quality of an image that is picked up is degraded due to diffraction.

To prevent the degradation of image quality, it is necessary to make an F-number of the objective optical system small. Consequently, in objective optical systems in recent years, a depth of field tends to be narrow. As a method of securing the depth of field of a wide range according to such image pickup element, a method of imparting a focusing function to the optical system is available. Optical systems having the focusing function have been proposed in Japanese Patent Publication No. 4819969, Japanese Patent Application Laid-open Publication No. 2012-37768, and Japanese Patent Publication No. 5607278.

SUMMARY OF THE INVENTION

The present invention provides the following means. In the following description, all values of focal length are about an e-line An objective optical system for endoscope includes order from an object side, a first group having a negative refractive power, a second group having a positive refractive power, and a third group having a positive refractive power, wherein the third group includes in order from the object side, a positive cemented lens and a positive lens, and observation from a normal observation state up to a close observation state is possible by moving the second group along an optical axis, and the first group includes a cemented lens, and the first group includes in order from the object side, a negative lens having a concave surface directed toward an image side, and the cemented lens, and the cemented lens is a negative cemented lens, and the second group includes a positive meniscus lens having a convex surface directed toward the object side, and the objective optical system for endoscope satisfies the following conditional expression (1).

$$4 \leq FB/f \leq 7 \quad (1)$$

where,

FB denotes a back focus of the objective optical system for endoscope, and f denotes a focal length of the overall objective optical system for endoscope in the normal observation state.

BRIEF DESCRIPTION OF THE DRAWINGS

FIG. 1A and FIG. 1B are diagrams showing a cross-sectional arrangement of an objective optical system for endoscope according to an embodiment of the present invention, where.

FIG. 2A and FIG. 2B are diagrams showing a cross-sectional arrangement of an objective optical system for endoscope according to an example 1 of the present invention, where.

FIG. 4A and FIG. 4B are diagrams showing a cross-sectional arrangement of an objective optical system for endoscope according to an example 2 of the present invention, where.

FIG. 6A and FIG. 6B are diagrams showing a cross-sectional arrangement of an objective optical system for endoscope according to an example 3 of the present invention, where.

FIG. 8A and FIG. 8B are diagrams showings cross-sectional arrangement of an objective optical system for endoscope according to an example 4 of the present invention, where.

DETAILED DESCRIPTION OF THE INVENTION

Reasons for adopting such arrangements and effects thereof in an objective optical system for endoscope according to the present embodiment will be described below by referring to the accompanying diagrams. However, the present invention is not limited to the embodiments described below.

Figure 1A:
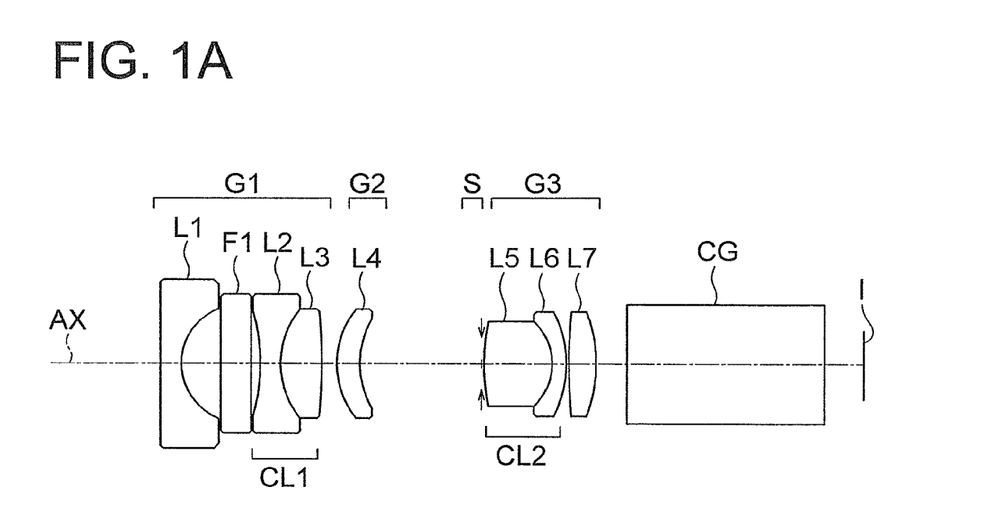
FIG. 1A is a cross-sectional view in a normal observation state.
Figure 1B:
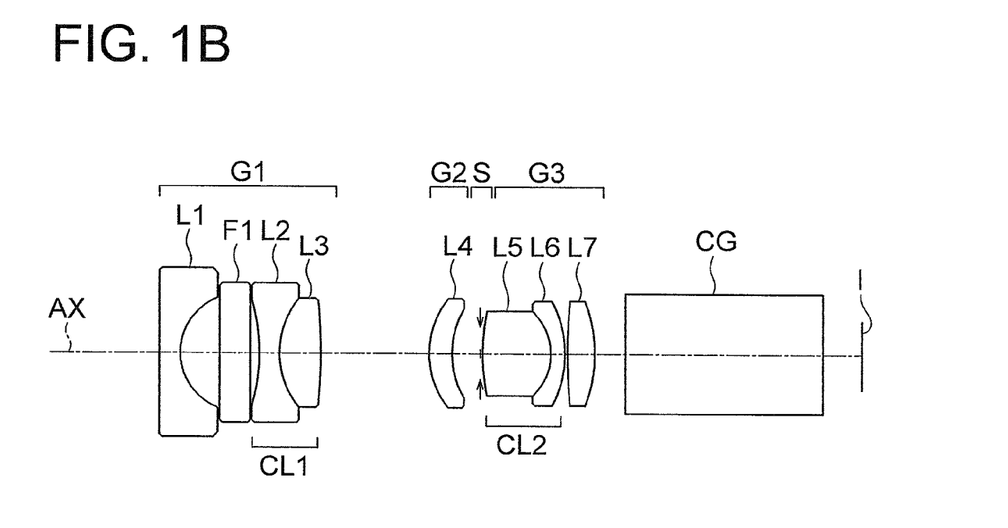
FIG. 1B is a cross-sectional view in a close observation state.

FIG. 1A and FIG. 1B are diagrams showing a cross-sectional arrangement of an objective optical system for endoscope according to the present embodiment. Here, FIG. 1A is a diagram showing a cross-sectional view of the objective optical system for endoscope in a normal observation state. Here, FIG. 1B is a diagram showing a cross-sectional view of the objective optical system for endoscope in a close observation state.

The objective optical system for endoscope according to the present embodiment includes in order from an object side, a first group G1 having a negative refractive power, a second group G2 having a positive refractive power, and a third group G3 having a positive refractive power. The third group G3 includes in order from the object side, a positive cemented lens CL2, and a positive lens L7. Observation from a normal observation state up to a close observation state is possible by moving the second group G2 along an optical axis, and the objective optical system for endoscope satisfies the following conditional expression (1).

$$4 \leq FB/f \leq 7 \quad (1)$$

where,

FB denotes a back focus of the objective optical system for endoscope, and f denotes a focal length of the overall objective optical system for endoscope in the normal observation state. Back Focus is a unit which is expressed upon air conversion of distance from the lens backmost surface to rear focal point.

The first group G1 having a negative refractive power is disposed nearest to object and a lens group having a positive refractive power is disposed on an image side thereof. Accordingly, it is possible to adopt an arrangement of retro focus type as an arrangement of an optical system. When the negative refractive power of the first group G1 is enhanced, it is possible to achieve a longer back focus. Therefore, it is preferable that the negative refractive power of the first group G1 is large.

The second group G2 having a positive refractive power is disposed on the image side of the first group G1. The second group G2 is a focusing group. Between the normal observation state and the close observation state, the second group G2 moves along the optical axis. The refractive power of the second group G2 has been set to be smaller than the refractive power of the third group G3. Consequently, it is possible to make small an amount of aberration that occurs in the second group G2 and an amount of fluctuation in aberration. Therefore, by moving the second group G2 having a positive refractive power, it is possible to carry out focusing with lesser aberration fluctuation.

The third group G3 having a positive refractive power is disposed on the image side of the second group G2. The third group G3 having a positive refractive power contributes mainly to image formation. Therefore, the refractive power of the third group G3 has been set to be larger than the refractive power of the second group G2. The positive cemented lens CL2 which includes a positive lens L5 and a negative lens L6 is disposed on the object side in the third group G3. By disposing the positive cemented lens CL2 on the object side it is possible to correct a longitudinal chromatic aberration favorably while maintaining the positive refractive power necessary for the image formation.

If the longitudinal chromatic aberration and a chromatic aberration of magnification are to be corrected in the third group G3, at least two cemented lenses are necessary. In the present embodiment, the third group G3, with regard to a chromatic aberration, corrects only the longitudinal chromatic aberration. For this, one cemented lens can serve the purpose. Accordingly, it is possible to form the optical system with a lesser number of lenses.

Moreover, an axial light beam and an off-axis light beam are separated. Therefore, the positive lens L7 is disposed at a position on the image side of the third group G3 where the off-axis light beam becomes high. Accordingly, it s possible to correct the off-axis aberration such as astigmatism and coma aberration.

In the present embodiment, as mentioned above, the first group G1 having a negative refractive power is disposed on the object side, the second group G2 having a positive refractive power and the third group G3 having a positive refractive power are disposed on the image side, and the positive lens is disposed nearest to image, and furthermore, conditional expression (1) is satisfied. Accordingly, it is possible to correct favorably an off-axis aberration such as a curvature of field and astigmatism with a lesser number of lenses while securing a long back focus, and to achieve a high-quality endoscopic image.

Next, conditional expression (1) will be described below. Conditional expression (1) regulates a ratio of the back focus and the focal length of the overall objective optical system for endoscope.

When an upper limit value of conditional expression (1) is exceeded, the back focus becomes excessively long with respect to the focal length of the overall objective optical system for endoscope. Consequently, all aberrations are deteriorated.

When a value falls below a lower limit value of conditional expression (1), an adequate back focus cannot be achieved. Consequently, it becomes difficult to dispose an optical member such as a prism in an optical path between the positive lens L7 disposed nearest to image and an image pickup element. The image pickup element, in FIG. 1A and FIG. 1B, is to be disposed at a position of an image plane I.

It is desirable to satisfy the following conditional expression (1') instead of conditional expression (1).

$$4.3 \leq FB/f \leq 6.4 \quad (1')$$

Furthermore, it is more desirable to satisfy the following conditional expression (1") instead of conditional expression (1).

$$4.6 \leq FB/f \leq 6.2 \quad (1'')$$

Moreover, in the present embodiment, it is desirable that the first group G1 includes a cemented lens CL1.

In the first group G1 disposed nearest to object, a height of an off-axis light ray becomes high. Therefore, the cemented lens CL1 is to be disposed in the first group G1. According to such arrangement, it is possible to correct the chromatic aberration of magnification favorably.

In the present embodiment, division of roles is such that, the first group G1 corrects the chromatic aberration of magnification and the third group G3 corrects the longitudinal chromatic aberration. In such manner, regarding the chromatic aberration, since the roles of aberration correction have been shared, it is possible to arrange the third group G3 with a lesser number of lenses. Therefore, even as the overall objective optical system for endoscope, it is possible to let the arrangement to secure a long back focus with a lesser number of lenses.

Moreover, in the present embodiment, it is desirable that the first group G1 includes in order from the order side, negative lens L1 having a concave surface directed toward the image side, and a cemented lens CL1, and the cemented lens CL1 is a negative cemented lens, and the second group G2 includes a positive meniscus lens L4 having a convex surface directed toward the object side. Moreover, it is desirable that the negative lens L1 is planoconcave lens.

As mentioned above, since an arrangement of retro-focus type is adopted as the arrangement of the optical system, the first group G1 is imparted the negative refractive power. Larger the negative refractive power, longer is the back focus that can be achieved, but an aberration is susceptible to occur. Therefore, the negative refractive power is let to be shared by the negative lens L1 and the cemented lens L2. The negative lens L1 is to be disposed nearest to object. The refractive power of the negative lens L1 is larger than the refractive power of the cemented lens CL1. Thus, in the present embodiment, the negative refractive power of the first group G1 is mainly let to be shared the negative lens L1.

On the image side of the negative lens L1, a marginal light ray passes through a high position. Therefore, the cemented lens CL1 is disposed on the image side of the negative lens L1. By disposing the cemented lens CL1 at this position, a lens diameter is not let to be large while correcting an aberration of the negative lens L1.

Moreover, the cemented lens CL1 as a whole has a shape of which a convex surface is directed toward the image side. The cemented lens CL1 is formed by cementing a negative lens L2 having a concave surface directed toward the object side and a positive lens L3. Accordingly, it is possible to correct the chromatic aberration of magnification favorably while maintaining the negative refractive power (power) which is necessary for achieving a long back focus.

Furthermore, a positive meniscus lens L4 is disposed on the image side of the cemented lens CL1. The positive meniscus lens L4 is arranged to face the convex surface toward the object side. Moreover, the positive meniscus lens L4 is a lens in the second group G2, and is a lens group to be moved at the time of focusing. As mentioned above, the positive refractive power of the second group G2 has been set to be small. Accordingly, it is possible to suppress an aberration fluctuation accompanying the focusing to be small.

Moreover, in the present embodiment, it is desirable to satisfy the following conditional expression (2).

$$8 \leq |f_{c1}/f| 23\ 22 \tag{2}$$

where, $f_{c1}$ denotes a focal length of the cemented lens in the first group G1, and f denotes the focal length of the overall objective optical system for endoscope in the normal observation state.

Conditional expression (2) regulates a ratio of the focal length of the cemented lens CL1 in the first group G1 and the focal length of the overall objective optical system for endoscope in the normal observation state. By satisfying conditional expression (2), it is possible to correct the chromatic aberration of magnification favorably while maintaining the negative refractive power necessary for achieving a long back focus.

When an upper limit value of conditional expression (2) is exceeded, the negative refractive power of the cemented lens CL1 in the first group G1 becomes small. Consequently, it becomes difficult to secure a long back focus.

When a value falls below a lower limit value of conditional expression (2), the negative refractive power of the cemented lens CL1 in the first group G1 becomes large. Consequently, correction of the chromatic aberration of magnification is inadequate, and therefore it is not preferable.

It is desirable to satisfy the following conditional expression (2') instead of conditional expression (2).

$$9.2 \leq |f_{c1}/f| \leq 22 \tag{2'}$$

Furthermore, it is more desirable to satisfy the following conditional expression (2'') instead of conditional expression (2).

$$10.5 \leq |f_{c1}/f| \leq 22 \tag{2''}$$

Moreover, in the present embodiment, it is desirable to satisfy the following conditional expression (3).

$$1 \leq |f_{c1}/f_{c3}| \leq 2.8 \tag{3}$$

where, $f_{c1}$ denotes a focal length of the cemented lens CL1 in the first group G1, and $f_{c3}$ denotes a focal length of the positive cemented lens CL2 in the third group G3.

Conditional expression (3) regulates a ratio of the focal length of the cemented lens CL1 in the first group G1 and the focal length of the positive cemented lens CL2 in the third group G3. In the optical system of the present embodiment, the cemented lens CL1 in the first group G1 and the positive cemented lens CL2 in the third group G3 have a refractive power for forming a retro-focus type which is necessary for securing a long back focus while correcting the chromatic aberration of magnification and the longitudinal chromatic aberration respectively.

When an upper limit value of conditional expression (3) is exceeded, the refractive power of the cemented lens CL1 in the first group G1 becomes small. Consequently, it becomes difficult to secure a long back focus.

When a value falls below a lower limit value of conditional expression (3), the refractive power of the cemented lens CL1 in the first group G1 becomes large. This is advantageous for securing a long back focus. However, it becomes difficult to correct an aberration. Particularly, since a balance of the chromatic aberration of magnification and the longitudinal chromatic aberration is disrupted, it is not preferable.

It is desirable to satisfy the following conditional expression (3') instead of conditional expression (3).

$$1.2 \leq |f_{c1}/f_{c3}| \leq 2.8 \tag{3'}$$

Furthermore, it is more desirable to satisfy the following conditional expression (3'') instead of conditional expression (3).

$$1.3 \leq |f_{c1}/f_{c3}| \leq 2.8 \tag{3''}$$

Moreover, in the present embodiment, it is desirable to satisfy the following conditional expression (4).

$$4 \leq f_{c3}/f \leq 12 \tag{4}$$

where, $f_{c3}$ denotes a focal length of the positive cemented lens CL2 in the third group G3, and f denotes the focal length of the overall objective optical system for endoscope in the normal observation state.

Conditional expression (4) regulates a ratio of the focal length, of the positive cemented lens CL2 in the third group G3 and the focal length of the overall objective optical system for endoscope in the normal observation state.

When an upper limit value of conditional expression (4) is exceeded, the refractive power of the positive cemented lens CL2 in the third group G3 becomes small. This is advantageous for securing a long back focus. However, since correction of the spherical aberration is excessive, it is not preferable.

When a value falls below a lower limit value of conditional expression (4), the refractive power of the positive cemented lens CL2 in the third group G3 becomes large. Consequently, it becomes difficult to secure a long back focus.

It is desirable to satisfy the following conditional expression (4') instead of conditional expression (4).

$$5.5 \leq f_{c3}/f \leq 10.5 \quad (4')$$

Furthermore, it is more desirable to satisfy the following conditional expression (4") instead of conditional expression (4).

$$7 \leq f_{c3}/f \leq 9 \quad (4'')$$

Moreover, in the present embodiment, it is desirable to satisfy the following conditional expression (5).

$$1 \leq |f_1/f| \leq 2.4 \quad (5)$$

where, $f_1$ denotes the focal length of the first group G1, and
f denotes the focal length of the overall objective optical system for endoscope in the normal observation state.

Conditional expression (5) regulates a ratio of the focal length of the first group G1 and the focal length of the overall optical system in the normal observation state.

When an upper limit value of conditional expression (5) is exceeded, the refractive power of the first group G1 becomes small. Consequently, it becomes difficult to secure a long back focus.

When a value falls below a lower limit value of conditional expression (5), the negative refractive power of the first group G1 becomes large. Consequently, correction of the curvature of field becomes excessive, and it is not preferable.

It is desirable to satisfy the following conditional expression (5') instead of conditional expression (5).

$$1.2 \leq |f_1/f| \leq 2.2 \quad (5')$$

Furthermore, it is more desirable to satisfy the following conditional expression (5") instead of conditional expression (5).

$$1.4 \leq |f_1/f| \leq 2.1 \quad (5'')$$

Moreover, in the present embodiment, it is desirable to satisfy the following conditional expression (6).

$$2.8 \leq f_3/f \leq 5.2 \quad (6)$$

where, $f_3$ denotes the focal length of the third group G3, and
f denotes the focal length of the overall objective optical system for endoscope in the normal observation state.

Conditional expression (6) regulates a ratio of the focal length of the third group G3 and the focal length of the overall objective optical system for endoscope in the normal observation state.

When an upper limit value of conditional expression (6) is exceeded, the refractive power of the third group G3 becomes small. This is advantageous for securing a long back focus. However, since correction of the curvature of field and spherical aberration becomes excessive, it is not preferable.

When a value falls below a lower limit value of conditional expression (6), the refractive power of the third group G3 becomes large. Therefore, when an attempt is made to secure a long back focus, all the aberrations are deteriorated.

It is desirable to satisfy the following conditional expression (6') instead of conditional expression (6).

$$3.1 f_3/f \leq 4.7 \quad (6')$$

Furthermore, it is more desirable to satisfy the following conditional expression (6") instead of conditional expression (6).

$$3.4 \leq f_3/f \leq 4.2 \quad (6'')$$

Moreover, in the present embodiment, it is desirable to satisfy the following conditional expression (7).

$$27 \leq f_2/f \leq 50 \quad (7)$$

where, $f_2$ denotes the focal length of the second group G2, and
f denotes the focal length of the overall objective optical system for endoscope in the normal observation state.

Conditional expression (7) regulates a ratio of the focal length of the second group G2 and the focal length of the overall objective optical system for endoscope in the normal observation state. The second group G2 is a lens group that moves at the time of focusing. For making small a fluctuation in aberration accompanying the movement of the moving lens group, it is necessary to make the refractive power of the moving lens group adequately small. For this, it is desirable to satisfy conditional expression (7).

When an upper limit value of conditional expression (7) is exceeded, it is advantageous for suppressing the fluctuation in aberration. However, it is necessary to move the second group G2 which is the moving lens group through a long distance along an optical axis AX. Consequently, the overall length of the objective optical system becomes long and it is not preferable.

When a value falls below a lower limit value of conditional expression (7), the refractive power of the second group G2 which is the moving lens group becomes large. Consequently, the fluctuation in aberration accompanying the movement of the second group G2 becomes large, and it is susceptible to cause degradation of image quality.

It is desirable to satisfy the following conditional expression (7') instead of conditional expression (7).

$$29 \leq f_2/f \leq 46 \quad (7')$$

Furthermore, it is more desirable to satisfy the following conditional expression (7") instead of conditional expression (7).

$$32 \leq f_2/f \leq 41 \quad (7'')$$

Moreover, in the present embodiment, it is desirable that the positive cemented lens CL2 in the third group G3 includes a positive lens L5, and satisfies the following conditional expression (8).

$$1.4 \leq D_{31}/f \leq 2.6 \quad (8)$$

where, $D_{31}$ denotes a thickness of the positive lens L5, and
f denotes the focal length of the overall objective optical system for endoscope in the normal observation state.

Conditional expression (8) regulates a ratio of the thickness of the positive lens L5 in the cemented lens CL2 of the third group G3 and the focal length of the overall objective optical system for endoscope in the normal observation state.

When an upper limit value of conditional expression (8) is exceeded, the thickness of the positive lens L5 in the cemented lens CL2 of the third group G3 becomes large. Consequently, the overall length of the optical system becomes long and it is not preferable.

When a value falls below a lower limit value of conditional expression (8), since an amount of astigmatism that occurs becomes large, it is not preferable.

It is desirable to satisfy the following conditional expression (8') instead of conditional expression (8).

$$1.5 \leq D_{31}/f \leq 2.4 \quad (8')$$

Furthermore, it is more desirable to satisfy the following conditional expression (8") instead of conditional expression (8).

$$1.7 \leq D_{31}/f \leq 2.2 \quad (8'')$$

Moreover, in the present embodiment, it is desirable that for the positive lens L5 in the positive cemented lens CL2 of the third group G3, a radius of curvature of an object-side surface is let to be larger than the radius of curvature of an image-side surface.

Moreover, in the present embodiment, it is desirable that the positive cemented lens CL2 in the third group G3 includes the positive lens L5, and satisfies the following conditional expression (9).

$$0.44 \leq (R_{31f}+R_{31r})/(R_{31f}-R_{31r}) \leq 0.67 \quad (9)$$

where, $R_{31f}$ denotes the radius of curvature of the object-side surface of the positive lens L5, and $R_{31r}$ denotes the radius of curvature of the image-side surface of the positive lens L5.

When either an upper limit value of conditional expression (9) is exceeded or a value falls below a lower limit value of conditional expression (9), since an amount of spherical aberration and coma aberration that occur becomes large, it is not preferable.

It is desirable to satisfy the following conditional expression (9') instead of conditional expression (9).

$$0.49 \leq (R_{31f}+R_{31r})/(R_{31f}-R_{31r}) \leq 0.66 \quad (9')$$

Furthermore, it is more desirable to satisfy the following conditional expression (9") instead of conditional expression (9).

$$0.53 \leq (R_{31f}+R_{31r})/(R_{31f}-R_{31r}) \leq 0.64 \quad (9'')$$

Moreover, in the present embodiment, it is desirable to satisfy the following conditional expression (10).

$$0.7 \leq f_{c3}/f_{33} \leq 2 \quad (10)$$

where, $f_{c3}$ denotes the focal length of the positive cemented lens CL2 in the third group G3, and $f_{33}$ denotes a focal length of the positive lens L7 in the third group G3.

Conditional expression (10) regulates a ratio of the focal length of the positive cemented lens CL2 in the third group G3, and the focal length of the positive lens L7 in the third group G3.

When an upper limit value of conditional expression (10) is exceeded, the refractive power of the positive cemented lens CL2 becomes small with respect to the refractive power of the positive lens L7 in the third group G3. Consequently, correction of the spherical aberration is excessive.

When a value falls below a lower limit value of conditional expression (10), the refractive of the positive cemented lens CL2 becomes large with respect to the refractive power of the positive lens L7 in the third group G3. Consequently, correction of the spherical aberration becomes inadequate, and therefore it is not preferable. Furthermore, since an amount of the longitudinal chromatic aberration that occurs becomes large, it is susceptible to cause degradation of image quality.

It is desirable to satisfy the following conditional expression (10') instead of conditional expression (10).

$$0.8 \leq f_{c3}/f_{33} \leq 1.8 \quad (10')$$

Furthermore, it is more desirable to satisfy the following conditional expression (10") instead of conditional expression (10).

$$1 \leq f_{c3}/f_{33} \leq 1.6 \quad (10'')$$

Moreover, for the positive lens L7 in the third group G3, it is desirable to let a radius of curvature of an object-side surface to be larger than a radius of curvature of an image-side surface.

Moreover, in the present embodiment, it is desirable to satisfy the following conditional expression (11).

$$0.1 \leq (R_{33f}+R_{33r})/(R_{33f}-R_{33r}) \leq 1 \quad (11)$$

where, $R_{33f}$ denotes the radius of curvature of the object-side surface of the positive lens L7 in the third group G3, and $R_{33r}$ denotes the radius of curvature of the image-side surface of the positive lens L7 in the third group G3.

Conditional expression (11) regulates a ratio of the radius of curvature of the object-side surface of the positive lens L7 in the third group G3 and the radius of curvature of the image-side surface of the positive lens L7 in the third group G3. When either an upper limit value of conditional expression (11) is exceeded or a value falls below a lower limit value of conditional expression (11) an amount of occurrence of the spherical aberration and the coma aberration becomes large, and it is not preferable.

It is desirable to satisfy the following conditional expression (11') instead of conditional expression (11).

$$0.25 \leq (R_{33f}+R_{33r})/(R_{33f}-R_{33r}) \leq 0.9 \quad (11')$$

Furthermore, it is more desirable to satisfy the following conditional expression (11") instead of conditional expression (11).

$$0.4 (R_{33f}+R_{33r})/(R_{33f}-R_{33r}) \leq 0.85 \quad (11')$$

Moreover, in the present embodiment, it is desirable that the positive cemented lens CL2 in the third group G3 includes a negative lens L6, and satisfies the following conditional expressions (12) and (13).

$$1.84 \leq Ne_{32} \quad (12)$$

$$35 \geq vd_{32} \quad (13)$$

where, $Ne_{32}$ denotes a refractive index about an e-line of the negative lens L6, and $vd_{32}$ denotes Abbe's number for the negative lens L6.

When a value falls below a lower limit value of conditional expression (12), the refractive power of the negative lens L6 in the cemented lens CL2 of the third group G3 becomes large Consequently, correction of the curvature of field is excessive, which is not preferable.

It is desirable to satisfy the following conditional expressions (12') and (13') instead of conditional expressions (12) and (13).

$$1.88 \leq Ne_{32} \quad (12')$$

$$32 \geq vd_{32} \quad (13')$$

Furthermore, it is more desirable to satisfy the following conditional expressions (12") and (13") instead of conditional expressions (12) and (13).

$$1.91 \leq Ne_{32} \quad (12")$$

$$29 \geq vd_{32} \quad (13")$$

Example 1

An objective optical system for endoscope according to an example 1 of the present invention will be described below.

Figure 2A:
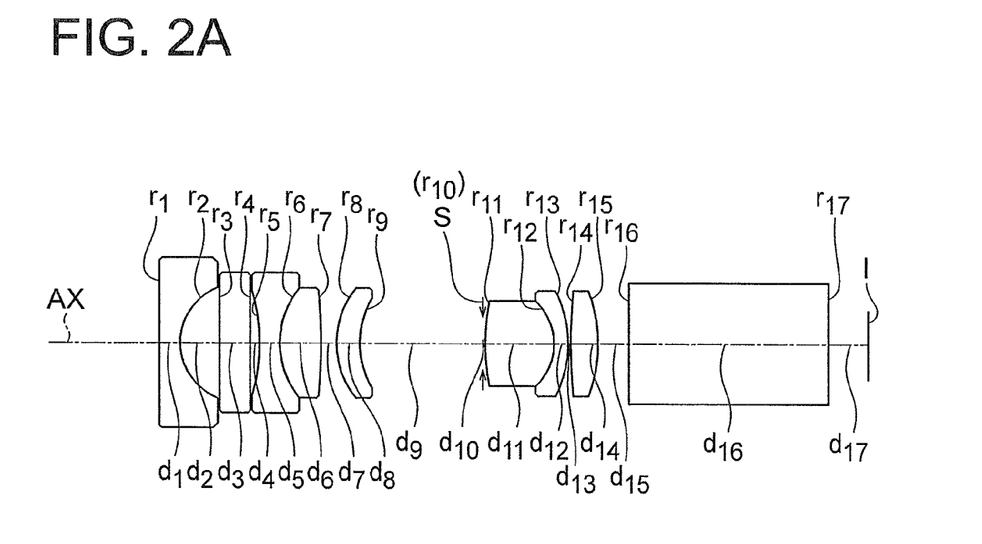
FIG. 2A is a cross-sectional view in a normal observation state and FIG. 2B is a cross-sectional view in a close observation state.
Figure 2B:
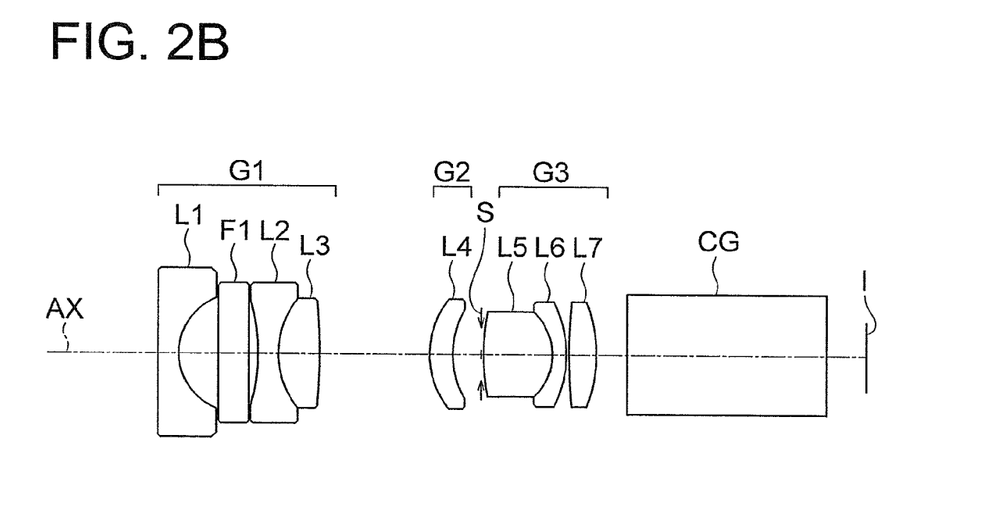
Figure 3A:
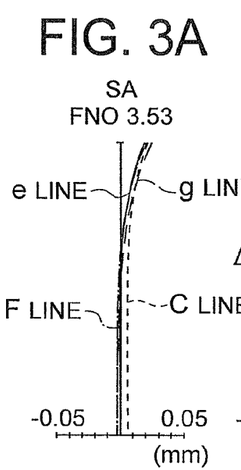
FIG. 3A, FIG. 3B, FIG. 3C, FIG. 3D, FIG. 3E, FIG. 3F, FIG. 3G, and FIG. 3H are aberration diagrams showing a spherical aberration (SA), an astigmatism (AS), a distortion (DT), and a chromatic aberration of magnification (CC) respectively of the example 1.
Figure 3B:
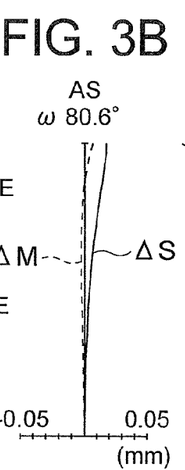
Figure 3C:
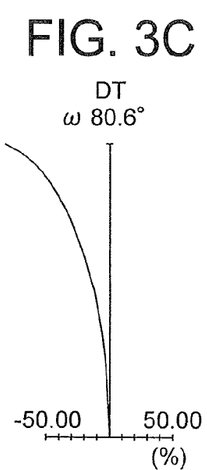
Figure 3D:
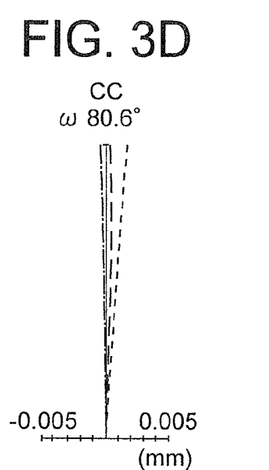
Figure 3E:
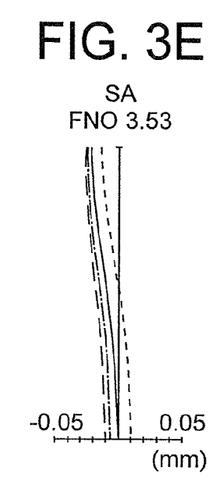
Figure 3F:
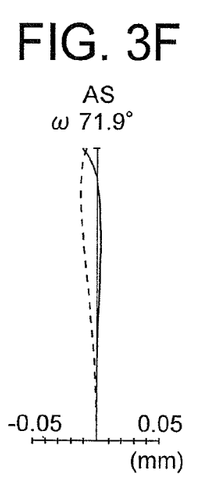
Figure 3G:
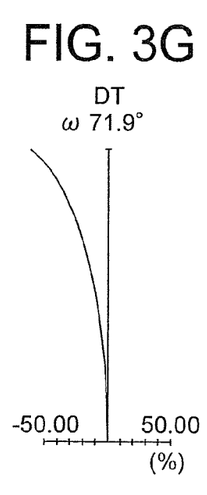
Figure 3H:
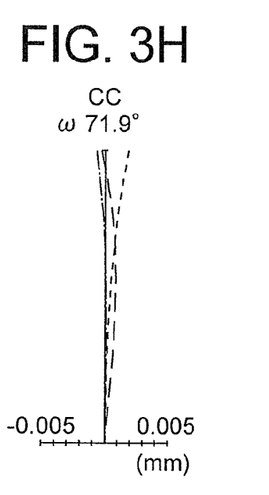

FIG. 2A is a cross-sectional view in a normal observation state (object point at a long distance) of the objective optical system for endoscope according to the example 1, and FIG. 2B is a cross-sectional view in a close observation state (object point at a close distance) of the objective optical system for endoscope according to the example 1.

The objective optical system for endoscope according to the example 1 includes in order from an object side, a first group G1 having a negative refractive power, a second group G2 having a positive refractive power, and a third group G3 having a positive refractive power. Moreover, an aperture stop S is fixed on an object side of the third group G3. The second group G2 moves toward an image side on an optical axis AX and corrects a change in a focal position due to a change from the normal observation state to the close observation state.

The first group G1 includes a planoconcave negative lens L1 having a concave surface directed toward the image side, plane-parallel plate F1, a biconcave negative lens L2, and a biconvex positive lens L3. The biconcave negative lens L2 and the biconvex positive lens L3 are cemented, and form a negative cemented lens CL1. The plane-parallel plate F1 is a filter with a coating applied thereon, for cutting light of a specific wavelength such as laser light of YAG (Yttrium Aluminum Garnet), laser of wavelength 1060 nm, laser light of semiconductor laser of wavelength 810 nm, or light of wavelength of near-infrared region.

The second group G2 includes a positive meniscus lens L4 having a convex surface directed toward the object side.

The third group G3 includes a biconvex positive lens L5, a negative meniscus lens L6 having a convex surface directed toward the image side, and a biconvex positive lens L7. The biconvex positive lens L5 and the negative meniscus lens L6 are cemented and form a positive cemented lens CL2.

A prism is disposed on the image side of the third group G3. An optical path is bent in a prism in an optical system. In all the examples from the example 1 to example 4, instead of bending the optical path with the prism, an optical path length equivalent to the prism is indicated in diagram by converting to a thickness of a cover glass CG with a linear optical path.

FIG. 3A, FIG. 3B, FIG. 3C, and FIG. 3D show a spherical aberration (SA), an astigmatism (AS), a distortion (DT), and a chromatic aberration of magnification (CC) in the normal observation state of the example 1.

FIG. 3E, FIG. 3F, FIG. 3G, and FIG. 3H show a spherical aberration (SA), an astigmatism (AS), a distortion (DT), and a chromatic aberration of magnification (CC) in the close observation state.

These various aberration diagrams show aberrations at wavelengths of 656.27 nm (C-line), 546.07 nm (e-line), 486.13 nm (F-line), and 435.84 nm (g-line). Moreover, in each diagram, ω denotes a half angle of view. Similar is the case for aberration diagrams below.

Example 2

An objective optical system for endoscope according to an example 2 of the present invention will be described below.

Figure 4A:
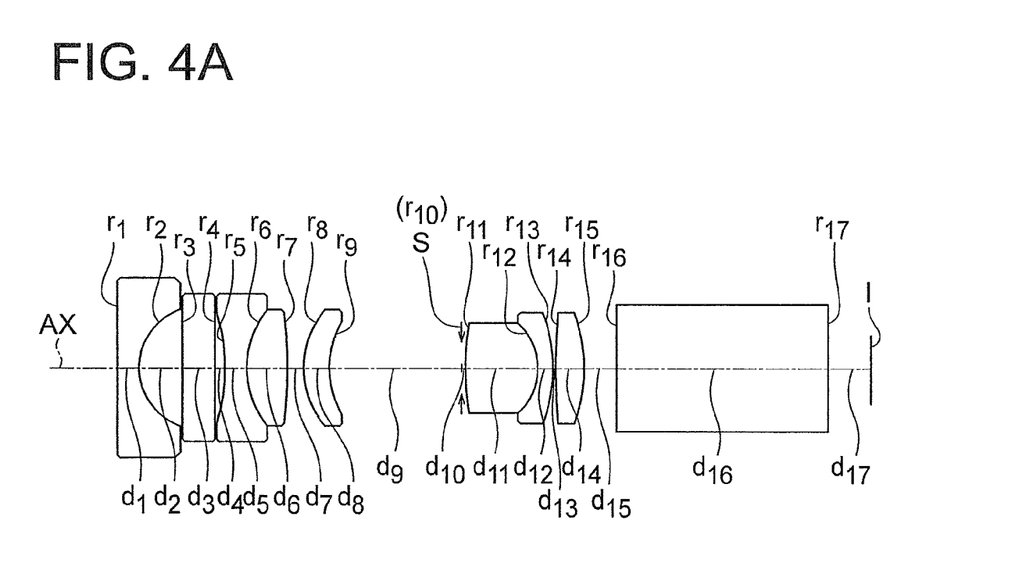
FIG. 4A is a cross-sectional view in a normal observation, state
Figure 4B:
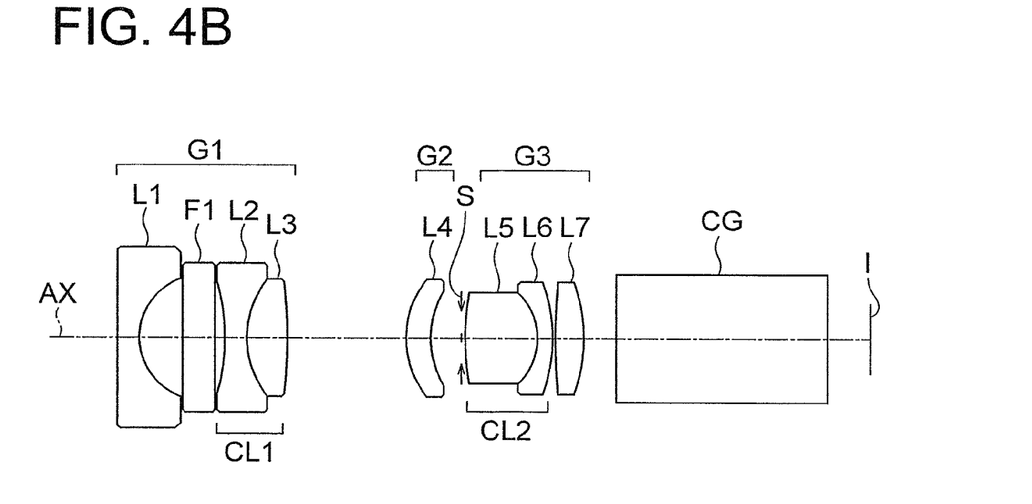
FIG. 4B is a cross-sectional view in a close observation state.
Figure 5A:
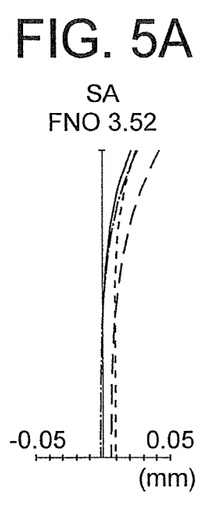
FIG. 5A, FIG. 5B, FIG. 5C, FIG. 5D, FIG. 5E, FIG. 5F, FIG. 5G, and FIG. 5H are aberration diagrams showing a spherical aberration (SA), an astigmatism (AS), a distortion (DT), and a chromatic aberration of magnification (CC) respectively of the example 2.
Figure 5B:
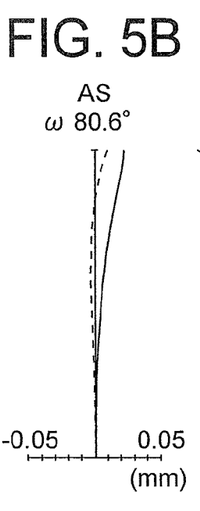
Figure 5C:
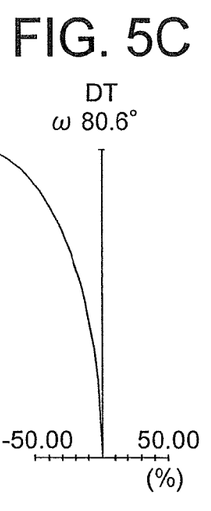
Figure 5D:
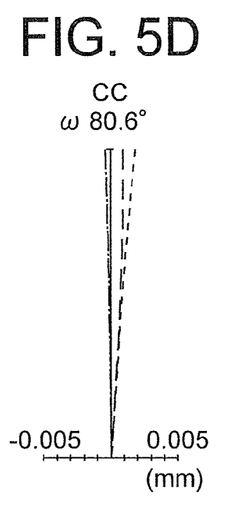
Figure 5E:
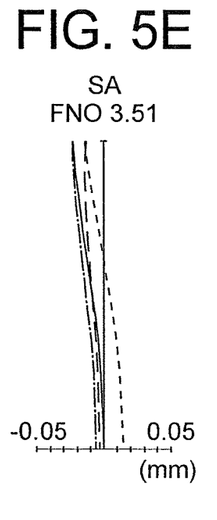
Figure 5F:
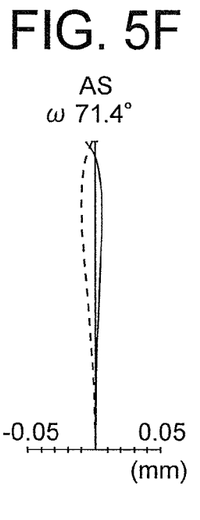
Figure 5G:
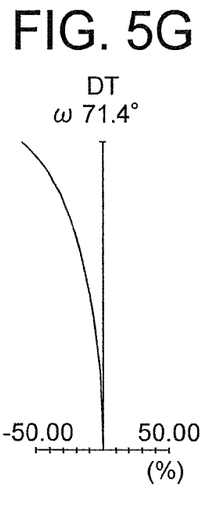
Figure 5H:
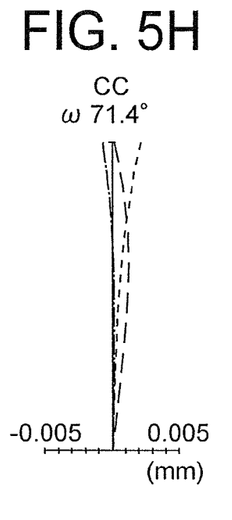

FIG. 4A is a cross-sectional view in a normal observation state (object point at a long distance) of the objective optical system for endoscope according to the example 2, and FIG. 4B is a cross-sectional view in a close observation state (object point at a close distance) of the objective optical system for endoscope according to the example 2.

The objective optical system for endoscope according to the example 2 includes in order from an object side, a first group G1 having a negative refractive power, a second group G2 having a positive refractive power, and a third group G3 having a positive refractive power. An aperture stop S is fixed on an object side of the third group G3. The second group G2 moves toward an image side on an optical axis AX and corrects a change in a focal position due to a change from the normal observation state to the close observation state.

The first group G1 includes a planoconcave negative lens L1 having a concave surface directed toward the image side, a plane-parallel plate F1, a biconcave negative lens L2, and a biconvex positive lens L3. The biconcave negative lens L2 and the biconvex positive lens L3 are cemented and form a negative cemented lens CL1. The plane-parallel plate F1 is a filter with a coating applied thereon, for cutting light of a specific wavelength such as laser light of YAG laser of wavelength 1060 nm, laser light of semiconductor laser of wavelength 810 nm, or light of wavelength of near-infrared region.

The second group G2 includes a positive meniscus lens L4 having a convex surface directed toward the object side.

The third group G3 includes a biconvex positive lens L5, a negative meniscus lens L6 having a convex surface directed toward the image side, and a biconvex positive lens L7. The biconvex positive lens L5 and the negative meniscus lens L6 are cemented and form a positive cemented lens CL2. A prism is disposed on the image side of the third group G3.

FIG. 5A, FIG. 5B, FIG. 5C, and FIG. 5D show a spherical aberration (SA), an astigmatism (AS), a distortion (DT), and a chromatic aberration of magnification (CC) in the normal observation state of the example 2.

FIG. 5E, FIG. 5F, FIG. 5G, and FIG. 5H show a spherical aberration (SA), an astigmatism (AS), a distortion (DT), and a chromatic aberration of magnification (CC) in the close observation state of the example 2.

Example 3

An objective optical system for endoscope according to an example 3 of the present invention will be described below.

Figure 6A:
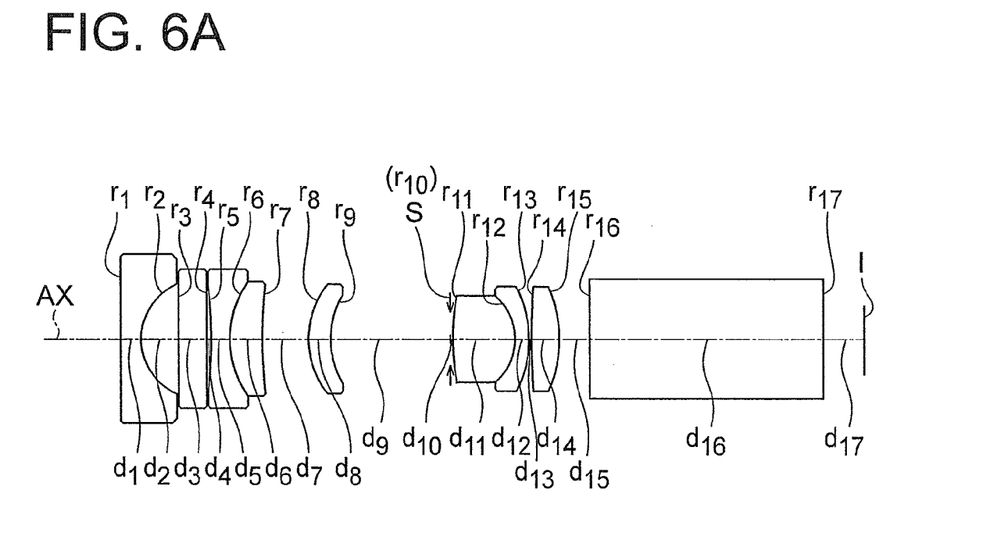
FIG. 6A is a cross-sectional view in a normal observation state and FIG. 6B is a cross-sectional view in a close observation state.
Figure 6B:
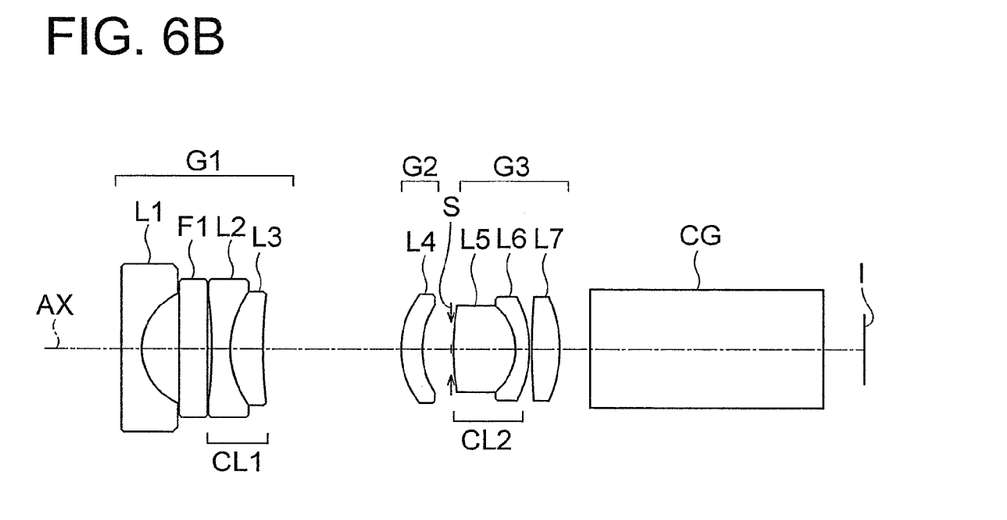
Figure 7A:
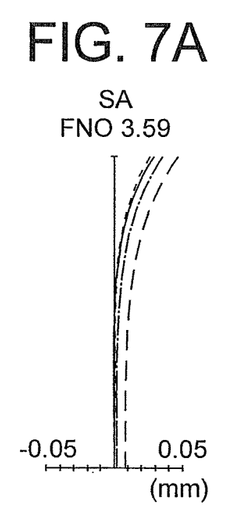
FIG. 7A, FIG. 7B, FIG. 7C, FIG. 7D, FIG. 7E, FIG. 7F, FIG. 7G, and FIG. 7H are aberration diagrams showing a spherical aberration (SA), an astigmatism (AS), a distortion (DT), and a chromatic aberration of magnification (CC) respectively of the example 3.
Figure 7B:
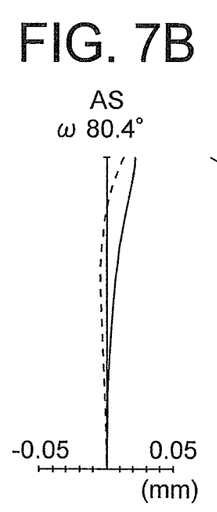
Figure 7C:
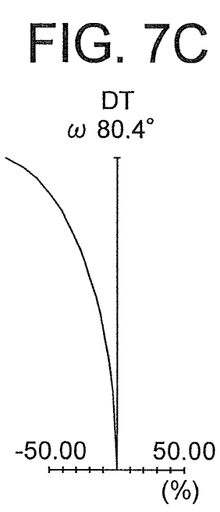
Figure 7D:
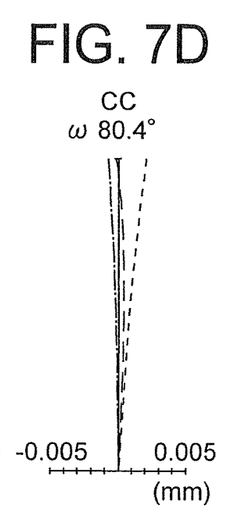
Figure 7E:
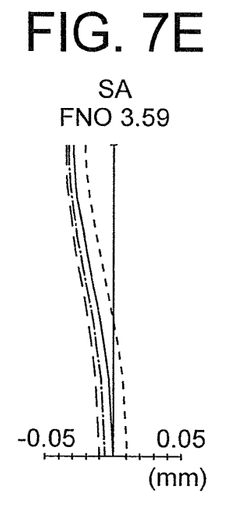
Figures 7F, 7G:
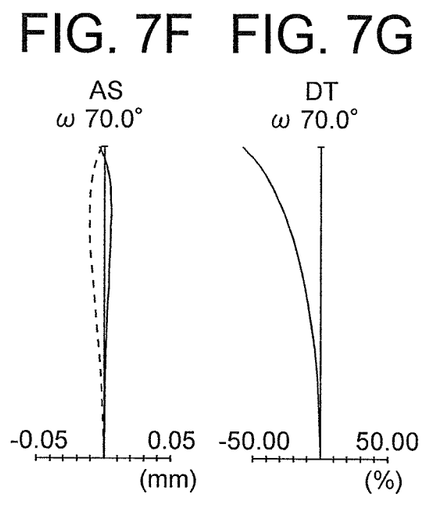
Figure 7H:
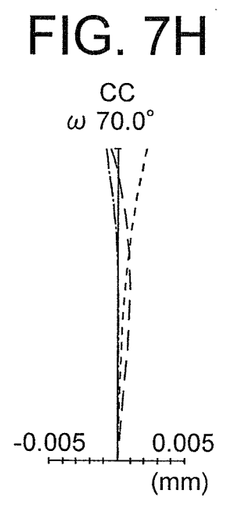

FIG. 6A is a cross-sectional view in a normal observation state (object point at a long distance) of the objective optical system for endoscope according to the example 3, and FIG. 6B is a cross-sectional view in a close observation state (object point at a close distance) of the objective optical system for endoscope according to the example 3.

The objective optical system for endoscope according to the example 3 includes in order from an object side, a first group G1 having a negative refractive power, a second group G2 having a positive refractive power, and a third group G3 having positive refractive power. An aperture stop S is fixed on the object side of the third group G3. The second group G2 moves toward an image side on an optical axis AX and corrects a change in a focal position due to a change from the normal observation state to the close observation state.

The first group G1 includes a planoconcave negative lens L1 having a concave surface directed toward the image side, a plane-parallel plate F1, a biconcave negative lens L2, and a positive meniscus lens L3 having a convex surface directed toward the object side. The biconcave negative lens L2 and the positive meniscus lens L3 are cemented and form a negative cemented lens CL1, The plane-parallel plate F1 is a filter with a coating applied, thereon, for cutting light of a specific wavelength such as laser light of YAG laser of wavelength 1060 nm, laser light of semiconductor laser of wavelength 810 nm, or light of wavelength of near-infrared region.

The second group G2 includes a positive meniscus lens L4 having a convex surface directed toward the object side.

The third group G3 includes a biconvex positive lens L5, a negative meniscus lens L6 having a convex surface directed toward the image side, and a biconvex positive lens L7. The biconvex positive lens L5 and the negative meniscus lens L6 are cemented and form a positive cemented lens CL2. A prism is disposed on the image side of the third group G3.

FIG. 7A, FIG. 7B, FIG. 7C, and FIG. 7D show a spherical aberration (SA), an astigmatism (AS), a distortion (DT), and a chromatic aberration of magnification (CC) in the normal observation state of the example 3.

FIG. 7E, FIG. 7F, FIG. 7G, and FIG. 7H show a spherical aberration (SA), an astigmatism (AS), a distortion (DT), and a chromatic aberration of magnification (CC) in the close observation state of the example 3.

Example 4

An objective optical system for endoscope according to an example 4 of the present invention will be described below.

Figure 8A:
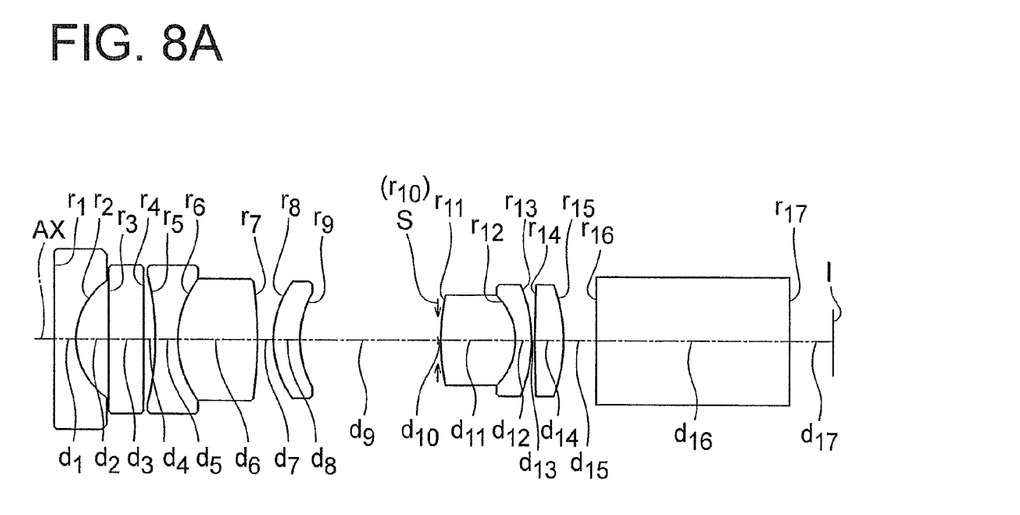
FIG. 8A is a cross-sectional view in a normal observation state and FIG. 8B is a cross-sectional view in a close observation state.
Figure 8B:
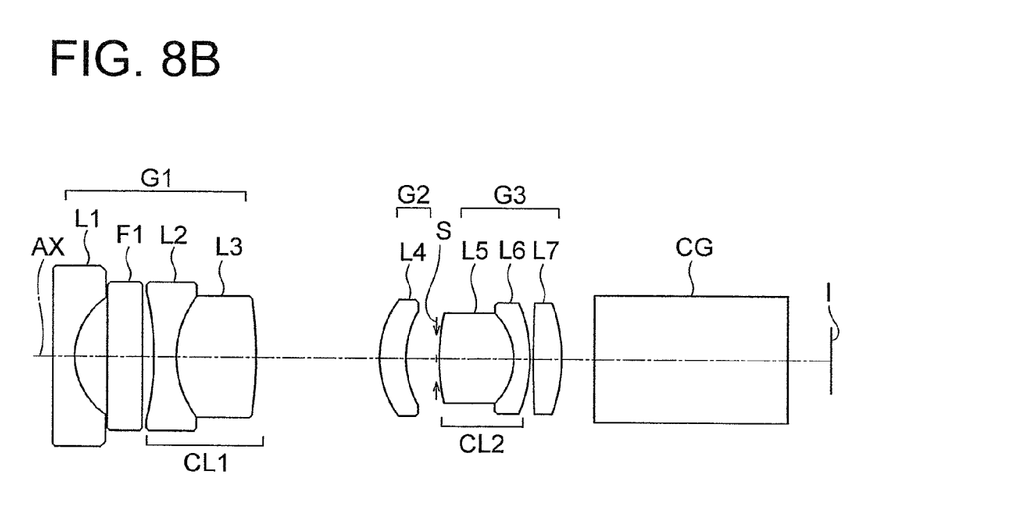
Figure 9A:
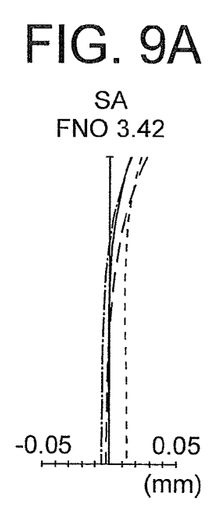
FIG. 9A, FIG. 9B, FIG. 9C, FIG. 9D, FIG. 9E, FIG. 9F, FIG. 9G, and FIG. 9H are aberration diagrams showing a spherical aberration (SA), an astigmatism (AS), a distortion (DT), and a chromatic aberration of magnification (CC) respectively of the example 4.
Figure 9B:
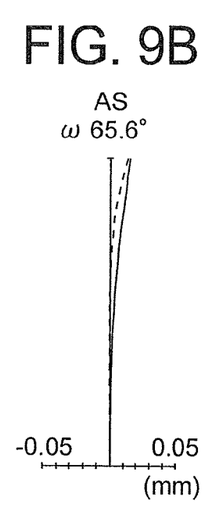
Figure 9C:
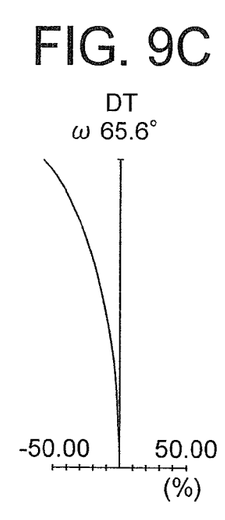
Figure 9D:
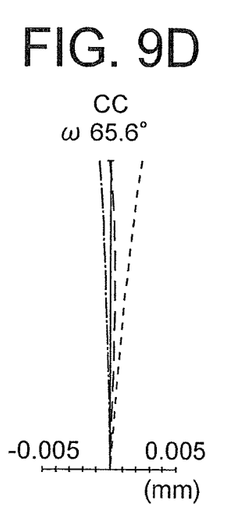
Figure 9E:
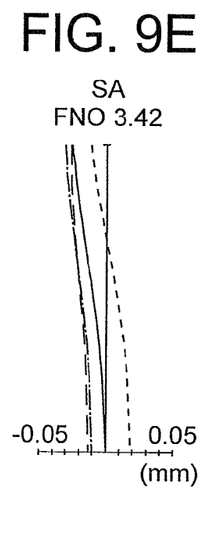
Figure 9F:
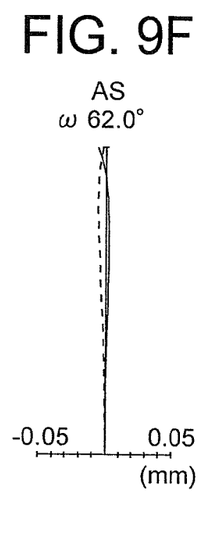
Figure 9G:
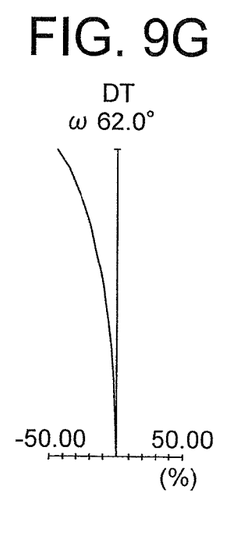
Figure 9H:
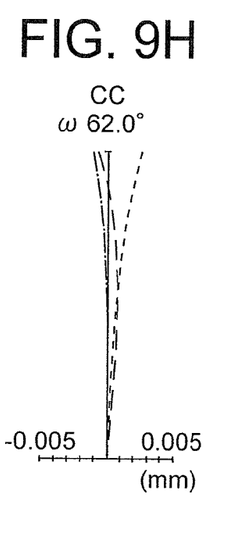

FIG. 8A is a cross-sectional view in a normal observation state (object point at a long distance) of the objective optical system for endoscope according to the example 4, and FIG. 8B is a cross-sectional view in a close observation state (object point at a close distance) of the objective optical system for endoscope according to the example 4.

The objective optical system for endoscope according to the example 4 includes in order from an object side, a first group G1 having a negative refractive power, a second group G2 having a positive refractive power, and a third group G3 having a positive refractive power. Moreover, an aperture stop S is fixed on the object side of the third group G3. The second group G2 moves toward an image side on an optical axis AX and corrects a change in a focal position due to a change from the normal observation state to the close observation state.

The first group G1 includes a planoconcave negative lens L1 having a concave surface directed toward the image side, a plane-parallel plate F1, a biconcave negative lens L2, and a biconvex positive lens L3. The biconcave negative lens L2 and the biconvex positive lens L3 are cemented and form a negative cemented lens CL1. The plane-parallel plate F1 is a filter with a coating applied thereon, for cutting light of a specific wavelength such as laser light of YAG laser of wavelength 1060 nm, laser light of semiconductor laser of wavelength 810 nm, or light of wavelength of near-infrared region.

The second group G2 includes a positive meniscus lens L4 having a convex surface directed toward the object side.

The third group G3 includes a biconvex positive lens L5, a negative meniscus lens L6 having a convex surface directed toward the image side, and a biconvex positive lens L7. The biconvex positive lens L5 and the negative meniscus lens L6 are cemented and form a positive cemented lens CL2.

A prism is disposed on the image side of the third group G3.

FIG. 9A, FIG. 9B, FIG. 9C, and FIG. 9D show a spherical aberration (SA), an astigmatism (AS), a distortion (DT), and a chromatic aberration of magnification (CC) in the normal observation state of the example 4.

FIG. 9E, FIG. 9F, FIG. 9G, and FIG. 9H show a spherical aberration (SA), an astigmatism (AS), a distortion (DT), and a chromatic aberration of magnification (CC) in the close observation state of the example 4.

Numerical data for each example is shown below. Here, r1, r2, . . . denote a radius of curvature of lens surfaces respectively, d1, d2, . . . denote a thickness and a distance between two lens surfaces, n1, n2, . . . denote refractive index for the e-line of lenses respectively, and ν1, ν2, . . . denote Abbe's number for the d-line of lenses respectively.

Numerical data for each example is shown below. Regarding the symbols, r denotes a radius of curvature of each lens, d denotes a distance between two lens surfaces, ne denotes a refractive index about the a-line of each lens, νd denotes Abbe's number for each lens, Fno denotes an F-number, and ω denotes a half angle of view. Moreover, as mentioned above, the focal length is a value about the e-line.

Example 1

| Unit mm | | | | |
|---|---|---|---|---|
| Surface data | | | | |
| Surface no. | r | d | ne | vd |
| Object plane | | d0(Variable) | | |
| 1 | ∞ | 0.396 | 1.88815 | 40.76 |
| 2 | 1.1938 | 0.7619 | | |
| 3 | ∞ | 0.594 | 1.51965 | 75.00 |
| 4 | ∞ | 0.1746 | | |
| 5 | −3.8364 | 0.4006 | 1.82017 | 46.62 |
| 6 | 1.7474 | 0.8067 | 1.85504 | 23.78 |
| 7 | −11.0669 | d1(Variable) | | |
| 8 | 1.7600 | 0.4510 | 1.62409 | 36.26 |
| 9 | 1.7806 | d2(Variable) | | |
| 10(Stop) | ∞ | 0.0515 | | |
| 11 | 4.2331 | 1.3358 | 1.57124 | 56.36 |
| 12 | −1.1682 | 0.2772 | 2.01169 | 28.27 |
| 13 | −2.2989 | 0.0495 | | |
| 14 | 10.8754 | 0.5384 | 1.51825 | 64.14 |
| 15 | −2.9156 | 0.5989 | | |
| 16 | ∞ | 3.861 | 1.73234 | 54.68 |
| 17 | ∞ | 0.792 | | |
| Image plane | ∞ | | | |

-continued

| Unit mm | | |
|---|---|---|
| Various data | | |
| | Normal observation state | Close observation state |
| IH | 0.654 | 0.654 |
| Fno. | 3.53 | 3.53 |
| ω(°) | 80.6 | 71.9 |
| d0 | 19.8 | 2.97 |
| d1 | 0.29898 | 2.16902 |
| d2 | 2.40541 | 0.53537 |

Example 2

| Unit mm | | | | |
|---|---|---|---|---|
| Surface data | | | | |
| Surface no. | r | d | ne | νd |
| Object plane | | d0(Variable) | | |
| 1 | ∞ | 0.42 | 1.88815 | 40.76 |
| 2 | 1.2521 | 0.8260 | | |
| 3 | ∞ | 0.63 | 1.51965 | 75.00 |
| 4 | ∞ | 0.1817 | | |
| 5 | −4.1214 | 0.4280 | 1.82017 | 46.62 |
| 6 | 1.8820 | 0.7833 | 1.85504 | 23.78 |
| 7 | −10.0004 | d1(Variable) | | |
| 8 | 1.8257 | 0.4916 | 1.62409 | 36.26 |
| 9 | 1.8399 | d2(Variable) | | |
| 10(Stop) | ∞ | 0.1045 | | |
| 11 | 5.3546 | 1.4025 | 1.62409 | 36.26 |
| 12 | −1.2390 | 0.2940 | 1.93429 | 18.90 |
| 13 | −3.1201 | 0.0525 | | |
| 14 | 12.3705 | 0.5540 | 1.62409 | 36.26 |
| 15 | −3.2966 | 0.6352 | | |
| 16 | ∞ | 4.095 | 1.73234 | 54.68 |
| 17 | ∞ | 0.84 | | |
| Image plane | ∞ | | | |

| Various data | | |
|---|---|---|
| | Normal observation state | Close observation state |
| IH | 0.694 | 0.694 |
| Fno. | 3.52 | 3.51 |
| ω(°) | 80.6 | 71.4 |
| d0 | 21.00000 | 3.15000 |
| d1 | 0.31710 | 2.31410 |
| d2 | 2.56634 | 0.56934 |

Example 3

| Unit mm | | | | |
|---|---|---|---|---|
| Surface data | | | | |
| Surface no. | r | d | ne | νd |
| Object plane | | d0(Variable) | | |
| 1 | ∞ | 0.392 | 1.88815 | 40.76 |
| 2 | 1.1978 | 0.7258 | | |
| 3 | ∞ | 0.539 | 1.51965 | 75.00 |
| 4 | ∞ | 0.0916 | | |
| 5 | −8.5445 | 0.3562 | 1.82017 | 46.62 |
| 6 | 2.0068 | 0.6236 | 1.93429 | 18.9 |
| 7 | 9.6984 | d1(Variable) | | |
| 8 | 1.7412 | 0.4266 | 1.85504 | 23.78 |
| 9 | 1.6907 | d2(Variable) | | |

| Unit mm | | | | |
|---|---|---|---|---|
| 10(Stop) | ∞ | 0.0434 | | |
| 11 | 4.8299 | 1.21 | 1.57392 | 52.95 |
| 12 | −1.1335 | 0.2744 | 2.01169 | 28.27 |
| 13 | −2.2552 | 0.049 | | |
| 14 | 14.3813 | 0.5466 | 1.48915 | 70.23 |
| 15 | −2.5615 | 0.5929 | | |
| 16 | ∞ | 4.508 | 1.73234 | 54.68 |
| 17 | ∞ | 0.784 | | |
| Image plane | ∞ | | | |

| Various data | | |
|---|---|---|
| | Normal observation state | Close observation state |
| IH | 0.648 | 0.648 |
| Fno. | 3.59 | 3.59 |
| ω(°) | 80.4 | 70.0 |
| d0 | 19.60000 | 2.94000 |
| d1 | 0.88860 | 2.68265 |
| d2 | 2.35204 | 0.55799 |

Example 4

| Unit mm | | | | |
|---|---|---|---|---|
| Surface data | | | | |
| Surface no. | r | d | ne | νd |
| Object plane | | d0(Variable) | | |
| 1 | ∞ | 0.44 | 1.88815 | 40.76 |
| 2 | 1.4956 | 0.6649 | | |
| 3 | ∞ | 0.715 | 1.51965 | 75.00 |
| 4 | ∞ | 0.229 | | |
| 5 | −5.8091 | 0.4486 | 1.88815 | 40.76 |
| 6 | 2.1545 | 1.6075 | 1.85504 | 23.78 |
| 7 | −9.0988 | d1(Variable) | | |
| 8 | 2.0446 | 0.5475 | 1.70442 | 30.13 |
| 9 | 2.0342 | d2(Variable) | | |
| 10(Stop) | ∞ | 0.1028 | | |
| 11 | 4.7908 | 1.5177 | 1.59667 | 35.31 |
| 12 | −1.3254 | 0.33 | 1.97189 | 17.47 |
| 13 | −3.0836 | 0.0722 | | |
| 14 | 32.9197 | 0.5799 | 1.70442 | 30.13 |
| 15 | −3.4904 | 0.6655 | | |
| 16 | ∞ | 3.9225 | 1.73234 | 54.68 |
| 17 | ∞ | 0.88 | | |
| Image plane | ∞ | | | |

| Various data | | |
|---|---|---|
| | Normal observation state | Close observation state |
| IH. | 0.727 | 0.727 |
| Fno. | 3.42 | 3.42 |
| ω(°) | 65.6 | 62.0 |
| d0 | 22.00000 | 3.30000 |
| d1 | 0.32602 | 2.52093 |
| d2 | 2.77813 | 0.58323 |

Values of the conditional expressions (1) to (13) of the examples 1, 2, 3 and 4 are shown below.
Conditional Expression

| | Example1 | Example2 | Example3 | Example4 |
|---|---|---|---|---|
| (1) FB/f | 5.43 | 5.40 | 6.04 | 4.78 |
| (2) $|f_{c1}/f|$ | 14.23 | 16.82 | 11.04 | 21.73 |
| (3) $|f_{c1}/f_{c3}|$ | 1.92 | 1.98 | 1.38 | 2.76 |
| (4) $f_{c3}/f$ | 7.40 | 8.49 | 8.00 | 7.86 |

-continued

|  |  | Example 1 | Example 2 | Example 3 | Example 4 |
|---|---|---|---|---|---|
| (5) | $|f_1/f|$ | 1.64 | 1.69 | 1.48 | 1.96 |
| (6) | $f_3/f$ | 3.84 | 3.81 | 3.96 | 3.62 |
| (7) | $f_2/f$ | 38.87 | 37.28 | 35.75 | 34.28 |
| (8) | $D_{31}/f$ | 2.01 | 1.97 | 1.84 | 1.90 |
| (9) | $(R_{31f}+R_{31r})/(R_{31f}-R_{31r})$ | 0.57 | 0.62 | 0.62 | 0.57 |
| (10) | $f_{c3}/f_{33}$ | 1.10 | 1.43 | 1.17 | 1.39 |
| (11) | $(R_{33f}+R_{33r})/(R_{33f}-R_{33r})$ | 0.58 | 0.58 | 0.70 | 0.81 |
| (12) | $Ne_{32}$ | 2.01 | 1.93 | 2.01 | 1.97 |
| (13) | $vd_{32}$ | 28.27 | 18.90 | 28.27 | 17.47 |

Various embodiments of the present invention have been described heretofore. However, the present invention is not limited only to the embodiments described above, and embodiments in which arrangements of these embodiments have been combined appropriately without departing from the scope of the invention are also within the scope of the present invention.

As described heretofore, the present invention is useful for an objective optical system for endoscope with a lesser number of lenses and high-performance optical characteristics, equipped with a long back focus and a focusing function, and in which the aberration fluctuation due to focusing is small.

An objective optical system for endoscope according to an embodiment of the present invention shows an effect that the objective optical system for endoscope is equipped with a long back focus and a focusing function, and has a lesser number of lenses and high-performance optical characteristics, and in which the aberration fluctuation accompanied by focusing is small.

What is claimed is:

1. An objective optical system for endoscope, comprising in order from an object side:
   a first group having a negative refractive power;
   second group having a positive refractive power; and
   a third group having a positive refractive power, wherein
   the third group includes in order from the object side, positive cemented lens and a positive lens, and
   observation from a normal observation state up to a close observation state is possible by moving the second group along an optical axis, and
   the first group includes a cemented lens, and
   the first group includes in order from the object side, a negative lens having a concave surface directed toward an image side, and the cemented lens, and
   the cemented lens is a negative cemented lens, and
   the second group includes a positive meniscus lens having a convex surface directed toward the object side, and
   the objective optical system for endoscope satisfies the following conditional expression (1)

$$4 \leq FB/f \leq 7 \quad (1)$$

where,
FB denotes a back focus of the objective optical system for endoscope, and
f denotes a focal length of the overall objective optical system for endoscope in the normal observation state.

2. The objective optical system for endoscope according to claim 1, wherein the objective optical system for endoscope satisfies the following conditional expression (2)

$$8 \leq |f_{c1}/f| \leq 22 \quad (2)$$

where,
$f_{c1}$ denotes a focal length of the cemented lens in the first group, and
f denotes the focal length of the overall objective optical system for endoscope in the normal observation state.

3. The objective optical system for endoscope according to claim 1, wherein the objective optical system for endoscope satisfies the following conditional expression (3)

$$1 \leq |f_{c1}/f_{c3}| \leq 2.8 \quad (3)$$

where,
$f_{c1}$ denotes a focal length of the cemented lens in the first group, and
$f_{c3}$ denotes a focal length of the positive cemented lens in the third group.

4. The objective optical system for endoscope according to claim 1, wherein the objective optical system for endoscope satisfies the following conditional expression (4)

$$4 \leq f_{c3}/f \leq 12 \quad (4)$$

where,
$f_{c3}$ denotes a focal length of the positive cemented lens in the third group, and
f denotes the focal length of the overall objective optical system for endoscope in the normal observation state.

* * * * *